United States Patent
Avitall et al.

(10) Patent No.: US 11,051,868 B2
(45) Date of Patent: *Jul. 6, 2021

(54) DISTAL BALLOON IMPEDANCE AND TEMPERATURE RECORDING TO MONITOR PULMONARY VEIN ABLATION AND OCCLUSION

(71) Applicant: Medtronic CryoCath LP, Toronto (CA)

(72) Inventors: Boaz Avitall, Chicago, IL (US); Catherine R. Condie, Shoreview, MN (US)

(73) Assignee: Medtronic CryoCath LP

( * ) Notice: Subject to any disclaimer, the term of this patent is extended or adjusted under 35 U.S.C. 154(b) by 122 days.

This patent is subject to a terminal disclaimer.

(21) Appl. No.: 16/517,150

(22) Filed: Jul. 19, 2019

(65) Prior Publication Data

US 2019/0365452 A1 Dec. 5, 2019

Related U.S. Application Data

(63) Continuation of application No. 15/688,107, filed on Aug. 28, 2017, now Pat. No. 10,376,299, which is a
(Continued)

(51) Int. Cl.
*A61B 18/02* (2006.01)
*A61B 18/00* (2006.01)

(52) U.S. Cl.
CPC ...... *A61B 18/02* (2013.01); *A61B 2018/0022* (2013.01); *A61B 2018/00404* (2013.01);
(Continued)

(58) Field of Classification Search
CPC ............ A61B 18/02; A61B 2018/0022; A61B 2018/00404; A61B 2018/00577;
(Continued)

(56) References Cited

U.S. PATENT DOCUMENTS

| 6,235,018 B1 | 5/2001 | LePivert |
| 7,914,525 B2 | 3/2011 | Abboud et al. |

(Continued)

FOREIGN PATENT DOCUMENTS

| WO | 2005081731 A2 | 9/2005 |
| WO | 2011136867 A1 | 11/2011 |

OTHER PUBLICATIONS

Supplementary European Search Report for Application No. EP 14 86 7560, dated Jun. 16, 2017, 6 pages.
(Continued)

*Primary Examiner* — George Manuel
(74) *Attorney, Agent, or Firm* — Christopher & Weisberg, P.A.

(57) ABSTRACT

A cryoablation method, system, and device that allows for real-time and accurate assessment and monitoring of PV occlusion and lesion formation without the need for expensive imaging systems and without patient exposure to radiation. The system includes a cryoballoon catheter with a cryoballoon, a distal electrode, a proximal electrode, and a temperature sensor. Impedance measurements recorded by the electrodes may be used to predict ice formation, quality of pulmonary vein occlusion, and lesion formation.

18 Claims, 9 Drawing Sheets

Related U.S. Application Data continuation of application No. 14/560,793, filed on Dec. 4, 2014, now Pat. No. 9,993,279.

(60) Provisional application No. 61/912,991, filed on Dec. 6, 2013.

(52) U.S. Cl.
CPC ........... *A61B 2018/00577* (2013.01); *A61B 2018/00684* (2013.01); *A61B 2018/00821* (2013.01); *A61B 2018/00875* (2013.01); *A61B 2018/0212* (2013.01); *A61B 2018/0268* (2013.01)

(58) Field of Classification Search
CPC ........... A61B 2018/00684; A61B 2018/00821; A61B 2018/00875; A61B 2018/0212; A61B 2018/0268
See application file for complete search history.

(56) References Cited

U.S. PATENT DOCUMENTS

| | | |
|---|---|---|
| 8,603,084 B2 | 12/2013 | Fish et al. |
| 2002/0072741 A1 | 6/2002 | Sliwa, Jr. et al. |
| 2004/0215294 A1 | 10/2004 | Littrup et al. |
| 2009/0182318 A1 | 7/2009 | Abboud et al. |
| 2011/0144524 A1* | 6/2011 | Fish ................ A61B 34/10 600/547 |
| 2012/0109115 A1 | 5/2012 | Condie et al. |
| 2012/0109118 A1 | 5/2012 | Lalonde et al. |
| 2012/0143179 A1 | 6/2012 | Avitall |
| 2012/0182318 A1 | 7/2012 | Mansfield et al. |
| 2012/0191080 A1 | 7/2012 | Markowitz |
| 2012/0197243 A1 | 8/2012 | Sherman et al. |
| 2013/0103020 A1 | 4/2013 | Levin |
| 2013/0238064 A1 | 9/2013 | Lafontaine |

OTHER PUBLICATIONS

International Search Report and Written Opinion dated Mar. 20, 2015, for corresponding International Application No. PCT/CA2014/000868; International Filing Date: Dec. 5, 2014, consisting of 16—pages.

European Patent Office, Communication pursuant to Article 94(3) EPC, for corresponding EP Application No. 14 867 560.6, dated Mar. 19, 2021, 5 pages.

* cited by examiner

DISTAL BALLOON IMPEDANCE AND TEMPERATURE RECORDING TO MONITOR PULMONARY VEIN ABLATION AND OCCLUSION

CROSS-REFERENCE TO RELATED APPLICATION

This application is a continuation of patent application Ser. No. 15/688,107, filed Aug. 28, 2017, entitled DISTAL BALLOON IMPEDANCE AND TEMPERATURE RECORDING TO MONITOR PULMONARY VEIN ABLATION AND OCCLUSION, and claims priority of patent application Ser. No. 14/560,793, filed Dec. 4, 2014, entitled DISTAL BALLOON IMPEDANCE AND TEMPERATURE RECORDING TO MONITOR PULMONARY VEIN ABLATION AND OCCLUSION, and is related to and claims priority to U.S. Provisional Patent Application Ser. No. 61/912,991, filed Dec. 6, 2013, entitled DISTAL BALLOON IMPEDANCE AND TEMPERATURE RECORDING TO MONITOR PULMONARY VEIN OCCLUSION, the entirety of which is incorporated herein by reference.

STATEMENT REGARDING FEDERALLY SPONSORED RESEARCH OR DEVELOPMENT n/a

TECHNICAL FIELD

The present invention relates to a cryoablation method, system, and device that allows for real-time and accurate assessment and monitoring of ice formation during pulmonary vein ablation using impedance measurements recorded by a distal electrode and a proximal electrode coupled to a cryotreatment device.

BACKGROUND

A cardiac arrhythmia is a condition in which the heart's normal rhythm is disrupted. Certain types of cardiac arrhythmias, including ventricular tachycardia and atrial fibrillation, may be treated by ablation (for example, radiofrequency (RF) ablation, cryoablation, ultrasound ablation, laser ablation, microwave ablation, and the like), either endocardially or epicardially.

Procedures such as pulmonary vein isolation (PVI) are commonly used to treat atrial fibrillation. This procedure generally involves the use of a cryogenic device, such as a catheter, which is positioned at the ostium of a pulmonary vein (PV) such that any blood flow exiting the PV into the left atrium (LA) is completely blocked. Once in position, the cryogenic device may be activated for a sufficient duration to create a desired lesion within myocardial tissue at the PV-LA junction, such as a PV ostium. If a cryoballoon is used as the treatment element of the cryogenic device, the balloon is typically inflated using a fluid coolant, enabling the balloon to create a circumferential lesion about the ostium and/or antrum of the PV to disrupt aberrant electrical signals exiting the PV.

The success of this procedure depends largely on the quality of the lesion(s) created during the procedure and whether the cryoballoon has completely occluded the PV. For example, a complete circumferential lesion is produced only when the cryoballoon has completely occluded the PV. Incomplete occlusion allows blood to flow from the PV being treated, past the cryoballoon, and into the left atrium of the heart. This flow of warm blood may prevent the cryoballoon from reaching temperatures low enough to create permanent lesions in the target tissue. The creation of reversible lesions may not be sufficient to achieve electrical isolation and, as a result, atrial fibrillation may be likely to reoccur. Additionally, even if the PV is completely occluded, suboptimal operation of the cryoablation system may result in cryoballoon temperatures that are not low enough, or not applied for a sufficient amount of time, to create permanent lesions in the target tissue.

Current methods of assessing or monitoring PV occlusion include fluoroscopic imaging of radiopaque contrast medium injected from the device into the PV. If the device, such as a cryoballoon catheter, has not completely occluded the PV ostium, some of the contrast medium may flow from the PV into the left atrium. In that case, the device may be repositioned and more contrast medium injected into the PV. This method not only necessitates the use of an auxiliary imaging system, but it also exposes the patient to potentially large doses of contrast medium and radiation. Alternatively, pressure measurement distal to the occlusion site can be used to assess occlusion prior to initiating the coolant injection. Other methods may involve the use of temperature sensors to determine the temperature within the cryoballoon and to correlate the measured temperature to a predicted thickness of ice created in tissue that is in contact with the cryoballoon. However, it may be difficult to accurately determine ice thickness based on balloon temperature alone and this latter method can only be used during coolant injection.

During cryoablation, ice forms between the cryoballoon and adjacent tissue, and this contributes to lesion formation. Additionally, ice formation between a cryotreatment element and adjacent tissue may be an indicator of PV occlusion. The greater the volume of warm blood that passes over the cryoballoon, the slower ice formation will occur, and the thinner the layer of the formed ice may be. However, direct means for measuring PV occlusion, ice formation, and/or ice thickness (and therefore PV ablation) are not available.

It is therefore desirable to provide a cryoablation method, system, and device that allows for real-time and accurate assessment and monitoring of ice formation during PV ablation without the need for expensive imaging systems and without patient exposure to radiation. It is further desirable to provide a means for using ice formation as an indicator of the presence and/or quality of PV ablation.

SUMMARY

The present invention advantageously provides a cryoablation method, system, and device that allows for real-time and accurate assessment and monitoring of PV ablation and occlusion without the need for expensive imaging systems and without patient exposure to radiation. The present invention further provides a means for using ice formation as an indicator of the presence and/or quality of PV ablation. The present invention also provides a cryoablation system and method that may accurately monitor lesion formation in real time, based on changes in the impedance measurements. A method of assessing lesion quality in pulmonary vein ostium tissue may include recording a first set of impedance measurements from an electrode on a balloon catheter having a treatment element at a distal portion, recording a second set of impedance measurements from the electrode, determining a first impedance slope using the first set of impedance measurements and determining a second impedance slope using the second set of impedance measurements, comparing the first slope to a first reference slope and the second slope to a second reference slope, and determining whether the balloon catheter is creating a permanent lesion in tissue surrounding the pulmonary vein (for example, a pulmonary vein antrum and/or ostium) based on the comparison of the first slope to the first reference slope and the second slope the second reference slope. Depending on the determination, the treatment element of the balloon catheter may be repositioned if lesion quality is poor (that is, if a permanent lesion is not being created in the tissue surrounding the pulmonary vein, such as pulmonary vein ostium tissue). The method may also include recording a set of temperature measurements and comparing the set of temperature measurements to the first slope and second slope of impedance measurements and comparing the set of temperature measurements to a reference temperature. The set of temperature measurements may be recorded from a thermocouple on the balloon catheter or the first electrode. The electrode may be located distal to the treatment element, such as at a location immediately distal to the treatment element. The electrode may be a first electrode, and the method may also include recording a first set of impedance measurements from a second electrode on the balloon catheter, recording a second set of impedance measurements from the second electrode, determining a third impedance slope using the first set of impedance measurements from the second electrode and determining a fourth impedance slope using the second set of impedance measurements from the second electrode, comparing the third slope and the fourth slope, comparing the first slope and the third slope, comparing the second slope and the fourth slope, and determining, based on the comparison between the first, second, third, and fourth slopes, whether the balloon catheter is creating a permanent lesion in the tissue pulmonary vein ostium tissue. Based on the determination, the treatment element may be repositioned until it is determined that the treatment element is creating a permanent lesion. The first electrode may be located distal to the treatment element, such as distal to and adjacent to the treatment element, and the second electrode may be located either distal to the first electrode or proximal to the treatment element. The thermocouple may be proximate the first electrode. The first slope and the second slope may at least partially define an impedance curve, and the impedance curve may represent impedance measured by at least the first electrode when the pulmonary vein is completely occluded. Further, the comparison between the first and second slopes may indicate a thickness of ice formed when the treatment element is activated. Further, determining whether the balloon catheter is creating a permanent lesion in the pulmonary vein tissue may include correlating the ice thickness to the creation of a permanent lesion by the balloon catheter. For example, a determination of permanent lesion formation may be made when the ice thickness is at least 3 mm or an impedance measured by the electrode is at least 2000Ω. As a further example, a determination of permanent lesion formation may be made when an impedance measured by the electrode is at least 2000Ω within 120±30 seconds.

A method of assessing pulmonary vein ostium lesion quality may include positioning a balloon catheter proximate a pulmonary vein ostium, the balloon catheter including a longitudinal axis and a balloon; reducing the temperature of the balloon to a temperature sufficient to ablate an ostium of the pulmonary vein; recording a first set of impedance measurements from each of a plurality of electrodes radially disposed about the longitudinal axis immediately distal to the balloon; recording a second set of impedance measurements from each of the plurality of electrodes; determining a first impedance slope using the first set of impedance measurements from each of the plurality of electrodes and determining a second impedance slope using the second set of impedance measurements from each of the plurality of electrodes; comparing the first impedance slope and the second impedance slope for each of the plurality of electrodes to generate an impedance curve for each of the plurality of electrodes; comparing the impedance curves of the plurality of electrodes to each other; determining, based on the comparison between the impedance curves, at least one of: whether the balloon catheter is creating a permanent lesion in the pulmonary vein ostium; whether the balloon catheter is not occluding the pulmonary vein; whether the balloon catheter is partially occluding the pulmonary vein; and whether the balloon catheter is completely occluding the pulmonary vein; determining, when the comparison indicates that the balloon catheter is partially occluding the pulmonary vein, a radial position of an area of the treatment element that is not in contact with tissue; and repositioning the treatment element until a determination of at least one of complete occlusion and the creation of a permanent lesion is made.

A method of determining cryoablation lesion quality may include: positioning a cryoballoon coupled to an ablation catheter in contact with a pulmonary vein ostium, the ablation catheter further including: a first electrode immediately distal to the cryoballoon; a second electrode distal to the first electrode; and at least one thermocouple proximate the first electrode, the first and second electrodes being within the pulmonary vein; initiating a flow of coolant within the cryoballoon to cool the cryoballoon to a temperature sufficient to ablate the pulmonary vein ostium; continuously recording impedance measurements from the first electrode; continuously recording impedance measurements from the second electrode; continuously recording temperature measurements from the thermocouple; and determining that a circumferential ablation lesion will be formed around the pulmonary vein ostium when the first electrode measures an impedance of at least 2000Ω and the thermocouple measures a temperature of −37.8±3.3° C. within 120±30 sec from the onset of the flow of coolant within the cryoballoon.

A system for cryoablating tissue may include: a cryoablation device, the device including: a balloon coupled to a distal portion of the device; a first electrode immediately distal to the balloon; a second electrode a distance from the first electrode; and at least one thermocouple proximate the first electrode; a source of coolant in fluid communication with the balloon; and a console including a processor, the processor programmed to: receive impedance measurements recorded by the first and second electrodes; receive temperature measurements recorded by the thermocouple; and determine whether the balloon is creating a permanent lesion in a pulmonary vein ostium, the determination based on at least one of the impedance measurements from the first electrode, impedance measurements from the second electrode, and temperature measurements from the at least one thermocouple. The processor may be further programmed to calculate a thickness of ice formed between the balloon and the pulmonary vein ostium and determine that the balloon will create a substantially circumferential lesion about the pulmonary vein ostium when the processor determines that the ice thickness is at least 3 mm. The second electrode may be proximal to the balloon, and the processor may be further programmed to compare impedance measured by the first electrode to impedance measured by the second electrode and determine whether the balloon is completely occluding the pulmonary vein based on the comparison between the impedance measured by the first electrode and the impedance measured by the second electrode.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1A:
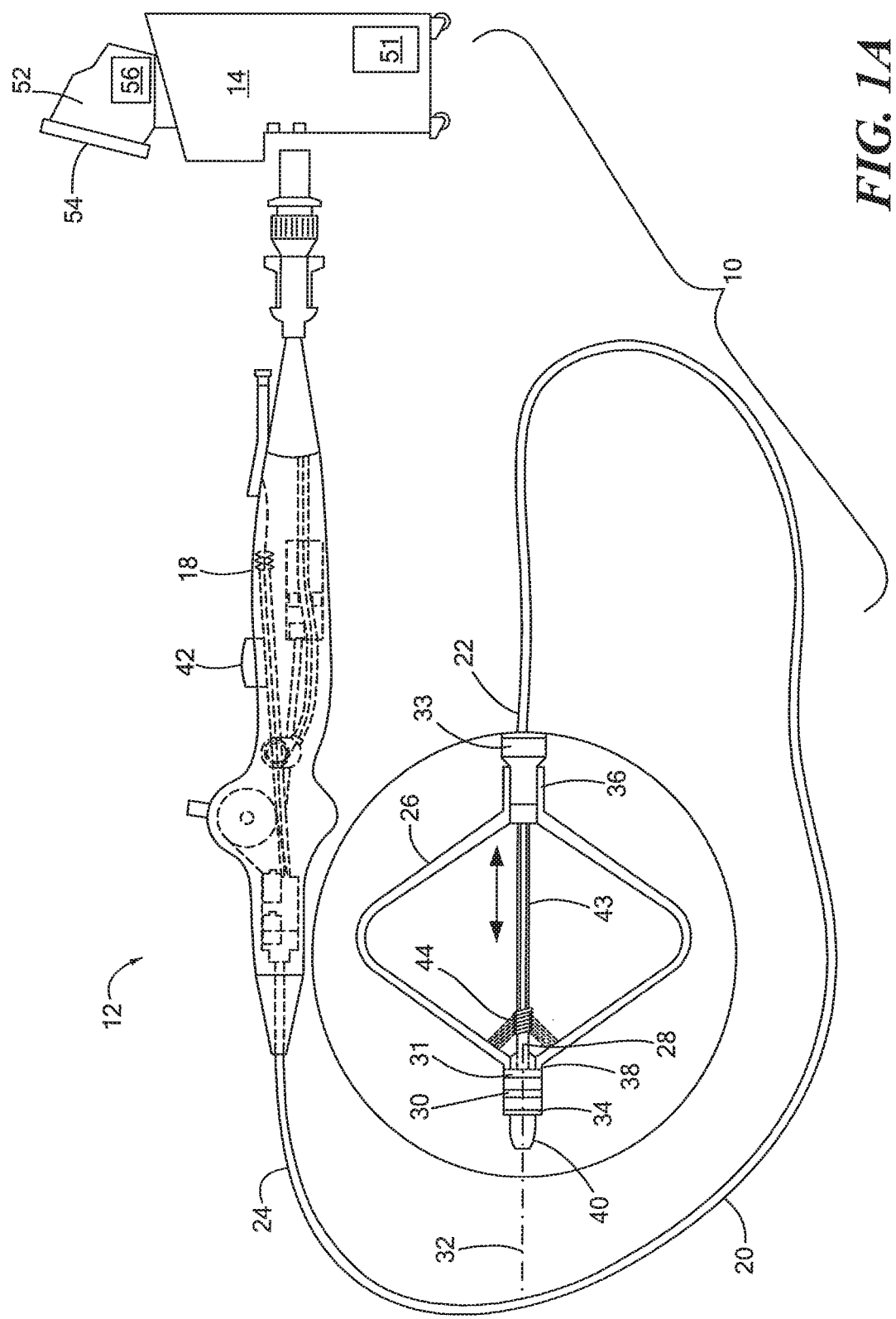
FIG. 1A shows an exemplary cryotreatment system including a first embodiment of a cryoballoon catheter.

Referring now to FIG. 1A, an exemplary cryotreatment system is shown. The system 10 may generally include a treatment device, such as a cryotreatment catheter 12, for thermally treating an area of tissue and a console 14 that houses various system 10 controls. The system 10 may be adapted for a cryotreatment procedure, such as cryoablation. The system 10 may additionally be adapted for radiofrequency (RF) ablation and/or phased RF ablation, ultrasound ablation, laser ablation, microwave ablation, hot balloon ablation, or other ablation methods or combinations thereof. The system 10 may also include a mapping catheter 16 (shown in FIG. 5) for sensing and recording electrical signals from tissue (for example, cardiac tissue).

The cryotreatment catheter 12 may generally include a handle 18, an elongate body 20 having a distal portion 22 and a proximal portion 24, one or more treatment elements 26, a shaft 28, a distal electrode 30, a proximal electrode 31, and a longitudinal axis 32. Each of the distal electrode 30 and proximal electrode 31 may be configured to measure both impedance and temperature. Alternatively, each electrode 30, 31 may measure impedance only. The device 12 may further include a reference electrode 33 and one or more temperature sensors 34, such as thermocouples for measuring temperature if the electrodes 30, 31 are not configured to measure temperature (as shown in FIG. 3). The treatment element 26 may be a cryoballoon, as shown in FIGS. 1A-4. The cryoballoon 26 may be coupled to the distal portion 22 of the elongate body 20 of the cryotreatment catheter 12. For example, the cryoballoon 26 may define a proximal portion or neck 36 that is affixed to or coupled to the distal portion 22 of the elongate body 20, and may further define a distal portion or neck 38 that is affixed to or coupled to the shaft 28 (such as the distal portion 40 of the shaft 28). However, it will be understood that the cryoballoon 26 may be coupled, affixed, disposed on, integrated with, or otherwise attached to the elongate body 20 and/or the shaft 28. Additionally, multiple cryoballoons may be used, such as when the cryoballoon 26 is disposed within or without a second cryoballoon (not shown). The shaft 28 may lie along the longitudinal axis 32 and be longitudinally movable within the elongate body 20. In this manner, longitudinal movement of the shaft 28 will affect the shape of the cryoballoon 26. The proximal portion of the shaft 28 may be in mechanical communication with one or more steering mechanisms 42 in the handle 18 of the cryotreatment catheter 12, such that the shaft 28 may be longitudinally extended or retracted using one or more steering mechanisms 42, such as knobs, levers, wheels, pull cords, and the like.

Figure 1B:
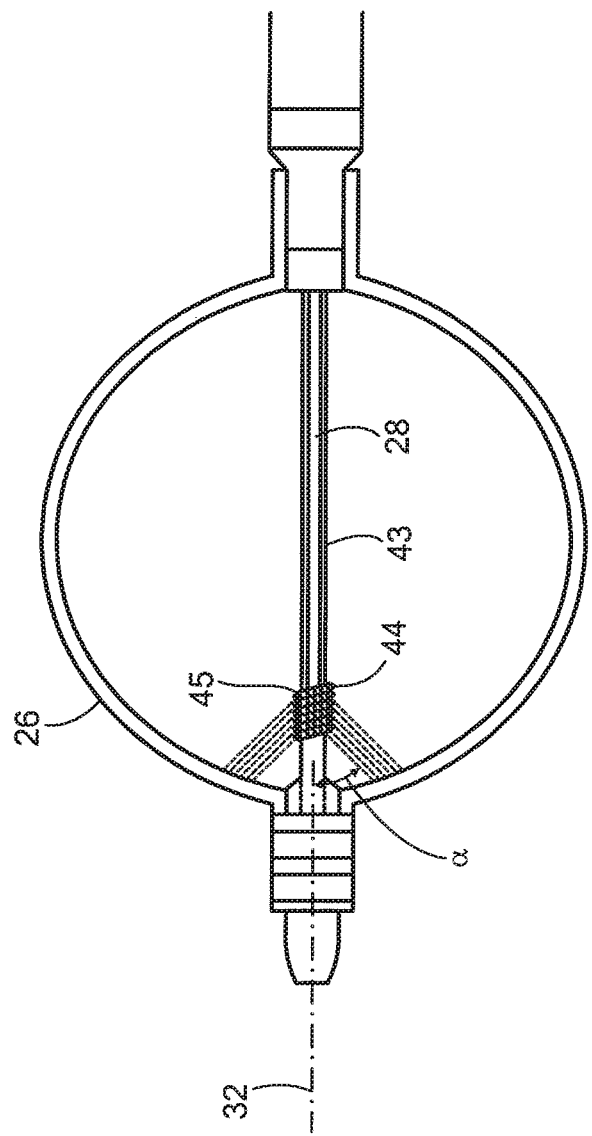
FIG. 1B shows a close-up, cross-sectional view of a distal portion of a cryoballoon catheter, with the delivery of coolant being directed toward the distal portion of the cryoballoon.

In addition to the shaft 28, the cryotreatment catheter 12 may include one or more lumens, such as a fluid injection lumen 43 and a fluid recovery lumen, for circulating coolant through from a fluid reservoir (which may be part of, disposed within, and/or in communication with the console 14) through the elongate body and to the cryoballoon 26, and for recovering expended coolant from the cryoballoon 26 and collecting the expended coolant within a fluid reservoir or venting to the atmosphere. Further, the cryotreatment catheter 12 may include a fluid delivery element 44 that is in fluid communication with the fluid injection lumen 43. As a non-limiting example, the fluid delivery element 44 may be wound about at least a portion of the shaft 28 within the cryoballoon 26, as shown in FIG. 1B. The fluid delivery element 44 may be configured to direct a spray of coolant toward the distal portion of the cryoballoon 26. For example, the fluid delivery element 44 may include a plurality of outlet ports 45 that are configured to deliver fluid at an angle α from the longitudinal axis 32 of the device, such as at an angle α of between approximately 30° and approximately 45° (±5°). However, it will be understood that the fluid delivery element 44 may have any configuration that is suitable for directing fluid toward the distal portion of the cryoballoon 26. If the cryotreatment catheter 12 includes thermoelectric cooling elements or electrodes capable of transmitting radiofrequency (RF), ultrasound, microwave, electroporation energy, or the like, the elongate body 18 may include a lumen in electrical communication with an energy generator (which may be part of, disposed within, and/or in communication with the console 14).

The mapping catheter 16 may be passable (longitudinally movable) through the shaft 28. The mapping catheter 16 may include one or more pairs of mapping elements 46, such as electrodes capable of sensing and recording electrograms from cardiac tissue. The one or more pairs of mapping elements 46 may be composed of metal or other electrically conductive material and may be affixed on an outer surface of the mapping catheter 16, integrated and flush with the body of the mapping catheter 16 (such that the mapping catheter has a smooth outer surface), may be areas of exposed electrically conductive material (for example, where an outer insulative layer has been removed), or may be otherwise affixed, coupled to, or integrated with the mapping catheter 16. The mapping catheter 16 may be in deformable and/or steerable using one or more steering mechanisms 42 into a variety of configurations. For example, the distal of the mapping catheter 16 may be deformable into a lasso-type configuration, such that the loop portion 50 and mapping elements 46 may be in contact with at least a portion of an inner circumference of a PV.

The console 14 may be in electrical and fluid communication with the cryotreatment catheter 12 and the mapping catheter 16, and may include one or more fluid (for example, cryotreatment coolant) reservoirs, coolant recovery reservoirs, energy generators 51, and computers 52 with displays 54, and may further include various other displays, screens, user input controls, keyboards, buttons, valves, conduits, connectors, power sources, processors, and computers for adjusting and monitoring system 10 parameters. As used herein, the term "computer" may refer to any programmable data-processing unit, including a smart phone, dedicated internal circuitry, user control device, or the like. The computer 52 may include one or more processors 56 that are in electrical communication with the one or more pairs of mapping elements 46, the one or more electrodes 30, 31, the one or more treatment elements 26, and one or more valves and programmable to execute an algorithm for locating one or more optimal treatment areas, for controlling the temperature of the one or more treatment elements 26, for generating one or more displays or alerts to notify the user of various system criteria or determinations, and/or for predicting temperature within target tissue based at least in part on signals from one or more of the temperature sensors 34. As a non-limiting embodiment, the proximal portion of the mapping catheter 16 may include an electrical connection that is mateable to at least a portion of the console (for example, with the electrophysiology recording equipment) and in electrical communication with the one or more processors 56. Additionally, the electrodes 30, 31 may be in electrical communication with an energy generator 51 for the application of energy to the electrodes 30, 31 for sensing impedance and, optionally, for mapping cardiac electrograms from adjacent tissue.

The console 14 may also include one or more valves that are in electrical and/or mechanical communication with, and controllable by, the console 14. For example, the computer 52 and/or one or more processors 56 may be programmable to control various system components, such as the one or more valves, to operate according to a duty cycle that includes opening and closing the one or more valves to regulate the flow of coolant through the system 10 and the catheter 12, and to thereby regulate the temperature of the treatment element 26 (for example, the cryoballoon 26). The duty cycle may be programmable by the user and/or may be automatically set by the console 14 according to a predicted tissue temperature based at least in part on signals from one or more of the electrodes 30, 31, and/or temperature sensors 34.

Figure 2:
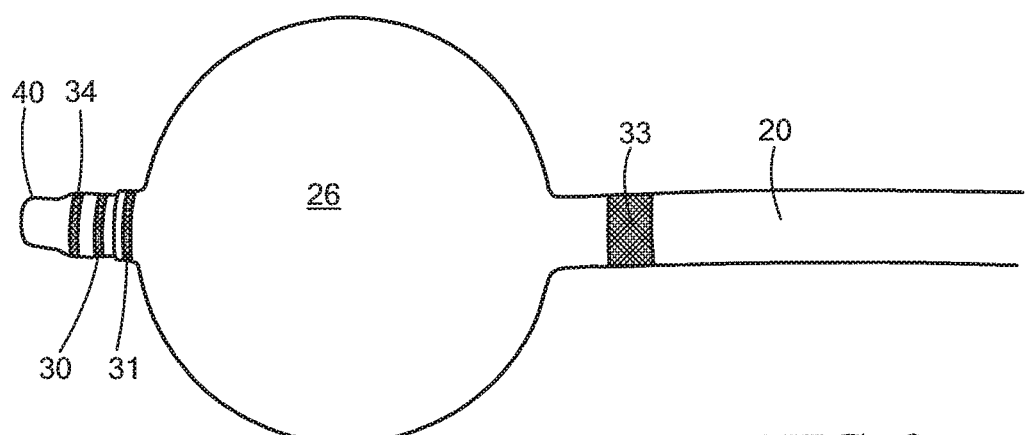
FIG. 2 shows a close-up view of the distal portion of the first embodiment of a cryoballoon catheter.
Figure 3:
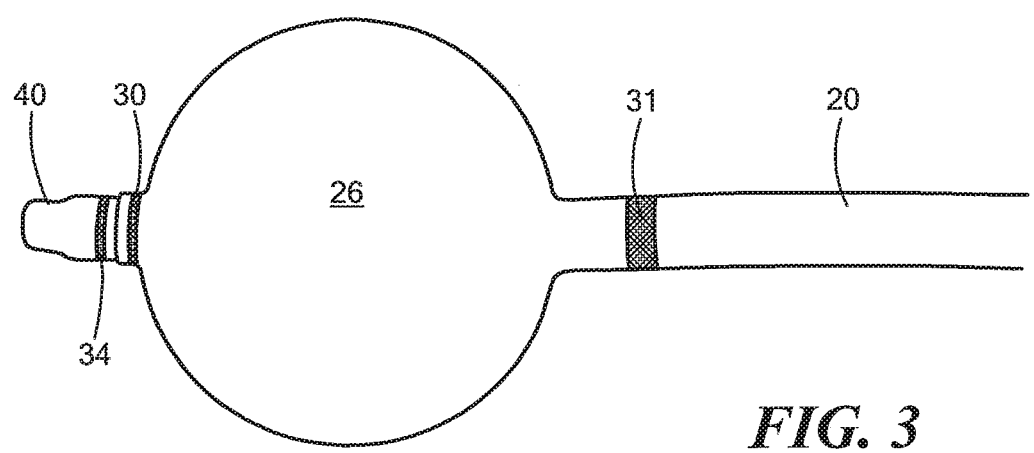
FIG. 3 shows a close-up view of the distal portion of a second embodiment of a cryoballoon catheter.

Referring now to FIG. 2, a close-up view of the distal portion of a first embodiment of the cryoballoon catheter is shown. As shown and described in FIGS. 1A and 1B, the cryotreatment device 12 may include one or more distal electrodes 30 and one or more proximal electrodes 31. The device 12 may further include a reference electrode 33 and one or more thermocouples 34 if the electrodes 30, 31 are not configured to measure temperature. The electrodes 30, 31, 33 may be composed of an electrically conductive material suitable for sensing impedance and, optionally, temperature. In the embodiment shown in FIGS. 1A-2, both electrodes 30, 31 and thermocouple 34 may be located distal to the cryoballoon 26. Electrodes 30, 31, 33 and thermocouple 34 may be coupled to, affixed to, disposed about, integrated with, or otherwise located on a distal portion of the device 12. The proximal electrode 31 may be located immediately distal to the cryoballoon 26, such as on the shaft distal portion 40. For example, the proximal electrode 31 may be adjacent to or abut the distal end of the cryoballoon 26. The distal electrode 30 may be located a distance from the proximal electrode 31. For example, the distal electrode 30 may be located approximately 2 mm distal to the proximal electrode 31. The cryotreatment device 12 may further include a thermocouple 34 for measuring temperature. The thermocouple 34 may be located a distance from the distal electrode 30. For example, the thermocouple 34 may be located approximately 2 mm distal to the distal electrode 30. Temperature monitoring may provide an additional and/or redundant means of assessing the quality of the freeze and propagation of the freeze in the tissue. As a non-limiting example, the balloon may have a diameter of approximately 23 mm to approximately 28 mm.

Alternatively, as shown in FIG. 3, the distal electrode 30 may be located immediately adjacent to the cryoballoon 26 and the proximal electrode 31 may be located proximal to the cryoballoon 26, such as on the elongate body distal portion 22. For example, the distal electrode 30 may be adjacent to or may abut the distal end of the cryoballoon 26. However, the proximal electrode 31 may alternatively be located on a sheath or a separate catheter. The proximal electrode 31 may be somewhat larger than the distal electrode 30, and may serve as the indifferent in a bipolar impedance circuit or reference electrode. The larger size of the proximal electrode 31 may minimize the impedance drop on the electrode 31, making the circuit more sensitive to change on the distal electrode 30. Since the electrode 31 is proximal to the cryoballoon 26, it may be more sensitive to occlusion changes because the direct electrical path through the blood pool is eliminated. The placement of electrodes 30, 31 shown in FIG. 3 additionally may allow the cryotreatment device 12 to be integrated with conventional electropotential navigation systems such as NavX, CARTO 3, and LocaLisa. Although not shown in FIGS. 2 and 4, the device 12 may also include a reference electrode 33 as shown and described in FIGS. 1A-2 and 5.

Figure 4:
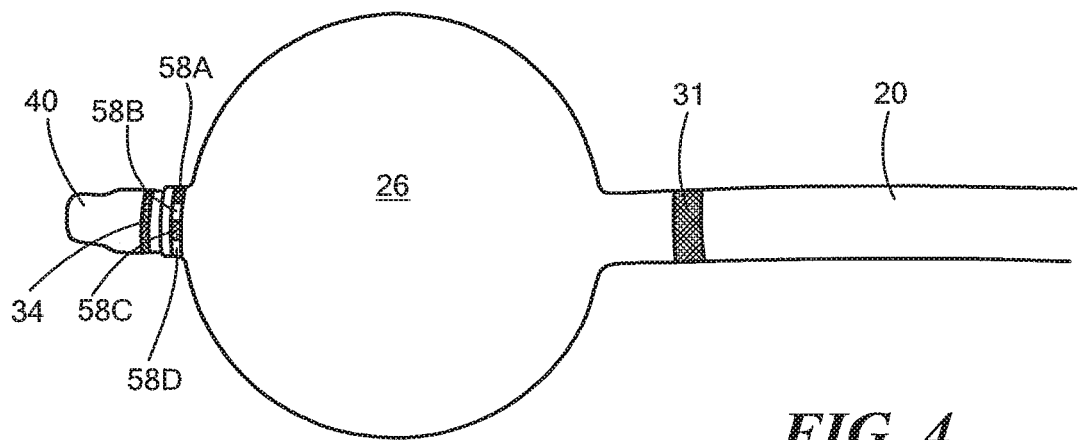
FIG. 4 shows a close-up view of the distal portion of a third embodiment of a cryoballoon catheter.

Referring now to FIG. 4, a close-up view of the distal portion of a second embodiment of a cryoballoon catheter is shown. The embodiment shown in FIG. 4 is generally similar to those shown in FIGS. 1A-3. Like the embodiment shown in FIGS. 1A-3, the cryotreatment device 12 shown in FIG. 4 may include a proximal electrode 31 that is located proximal to the cryoballoon 26. Instead of a distal electrode 30, however, the device 12 may include a plurality of discrete electrodes 58A, 58B, 58C, . . . radially disposed about the shaft distal portion 40 immediately distal to the cryoballoon 26. For example, each electrode 58 may be radially spaced about the longitudinal axis of the device and may be adjacent to or may abut the cryoballoon 26. Each electrode 58 may be monitored individually, allowing the user and/or console 14 to evaluate the symmetry of the impedance rise and therefore the ice formation. For example, a small leak of blood form the PV past one side of the cryoballoon 26 may result in a slower impedance rise on the electrode 58 closest to the leak. In addition to sensing impedance, the electrodes 30, 31, 58 of any embodiment may also be configured for mapping cardiac tissue (for example, recording cardiac electrograms) from adjacent tissue. In a non-limiting embodiment, the discrete electrodes 58 may be radially arranged in a distal housing coupled to the shaft distal portion 40, and each electrode 58 may protrude from the housing (for example, may be dome shaped) to facilitate local tissue depolarization for tissue mapping. Additionally or alternatively, the electrodes 58 may be used for electrical impedance tomography imaging to "see" the ice formation.

Regardless of the configuration of the electrodes (that is, whether the electrodes are as shown and described in FIGS. 1A-4), the fluid delivery element 44 may still direct fluid toward the distal end of the cryoballoon 26. In this way, ice may form more quickly on the one or more electrodes located distal to the cryoballoon 26.

Figure 5:
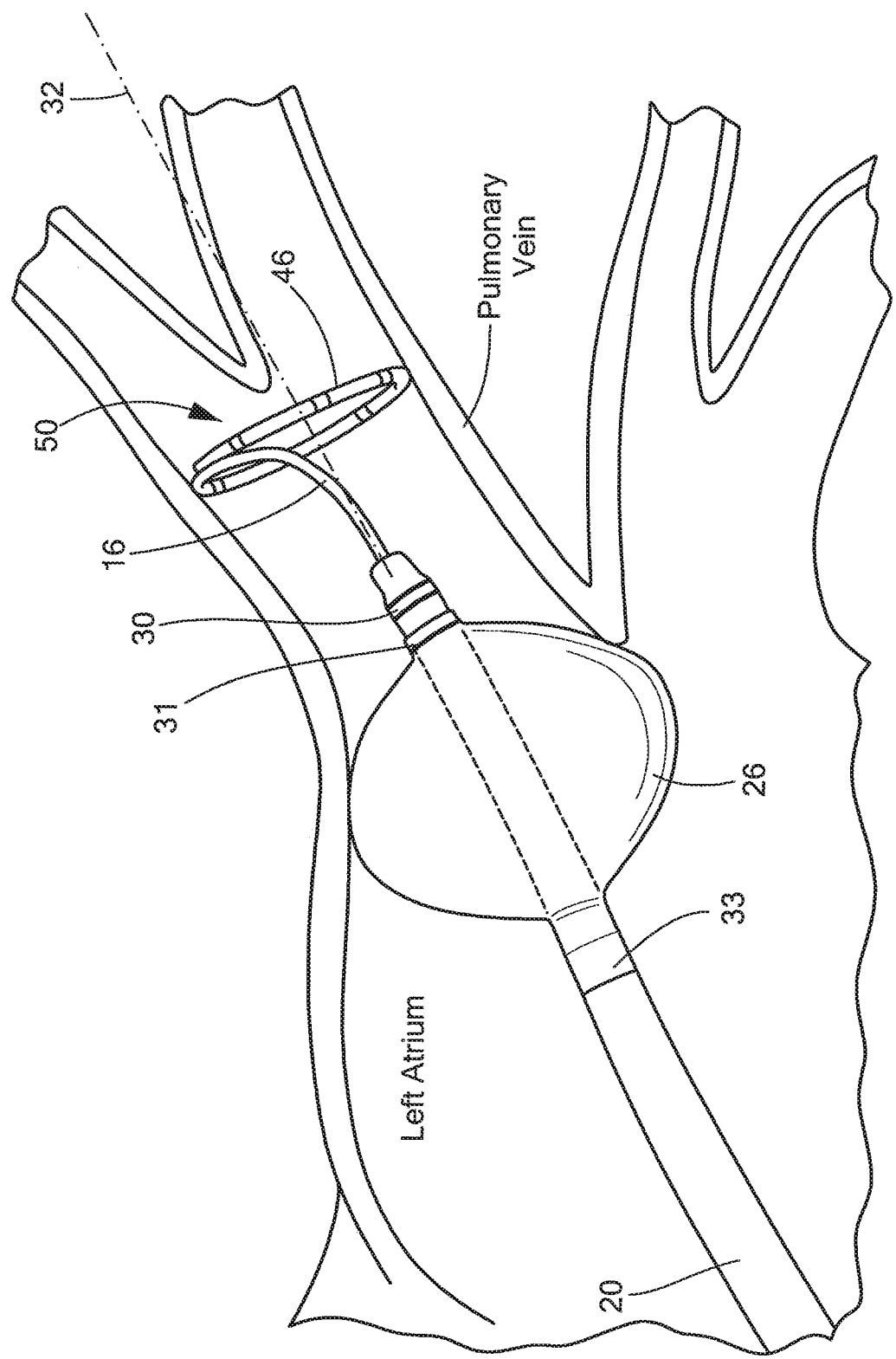
FIG. 5 shows a cryoballoon catheter within a heart.

Referring now to FIG. 5, a cryotreatment catheter is shown positioned proximate a pulmonary vein ostium for a pulmonary vein ablation procedure (which may also be referred to as a pulmonary vein isolation (PVI) procedure). As used herein, the term "PV tissue" or "pulmonary vein tissue" may include tissue of the PV ostium, the PV antrum, LA wall tissue, and/or tissue at the junction between the LA and PV, and is not limited to tissue within the PV. In fact, ablation of tissue within the PV may be undesirable. The inflated cryoballoon 26 may be positioned at the pulmonary vein (PV) ostium to occlude the PV, or block the flow of blood from the PV into the left atrium (LA) of the heart. Occlusion of the PV not only serves to position the cryoballoon 26 to create a circumferential lesion around the PV ostium, but also prevents warm blood from flowing over the portions of the cryoballoon 26 that are in contact with the target tissue, thereby enhancing the ability of the cryoballoon 26 to reach sufficiently cold temperatures for creating permanent, and circumferential, cryoablation lesions on or in the target tissue. If the PV is not completely occluded, blood flow past the cryoballoon 26 may have the effect of raising the temperature of the cryoballoon 26, possibly resulting in the formation of reversible lesions on or in the target tissue. The blocked blood within the PV may be referred to as "stagnant" blood, whereas the blood within the LA may be referred to as "flowing" blood, as blood may still enter the LA from the other three PVs that are not being occluded by the catheter 12.

As shown in FIG. 5, the cryoballoon 26 may be positioned at the PV ostium such that the shaft distal portion 40 is disposed within the PV, within the stagnant blood. Continuous impedance and temperature measurements may be taken during device placement and, subsequently, cryoablation. Impedance may increase as at least part of the cryoballoon 26 is inserted into the PV, which may indicate either full or partial occlusion. The amplitude of the impedance increase may be used to determine whether the occlusion is full or partial and, therefore, may be used to determine whether permanent lesions are being formed. For example, a greater amplitude may indicate full occlusion, whereas a lesser amplitude may indicate partial occlusion. Full occlusion may be indicative of permanent lesion formation as a result of the ablation procedure. If impedance and/or temperature measurements indicate that the PV is not permanently ablated and/or less than fully occluded, the device may be repositioned until complete PV occlusion is indicated by evaluation of the impedance and/or temperature measurements. For example, the one or more processors 56 of the console computer 52 may be programmed to receive and process data from the one or more electrodes and/or thermocouples, and to generate an alert to the user indicating that the device should be repositioned to achieve complete PV occlusion or that the device is already optimally positioned.

Figure 6A:
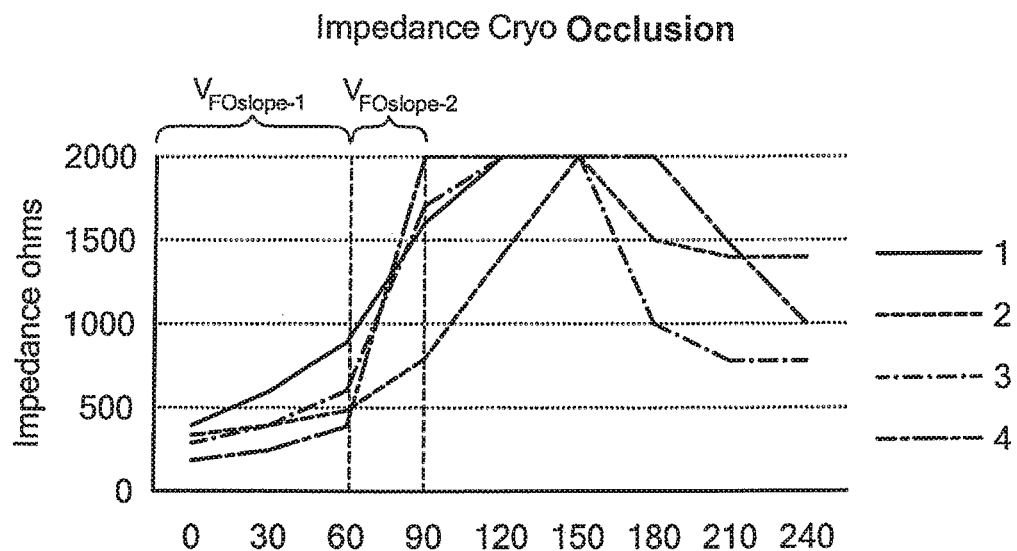
FIG. 6A show a graph illustrating change in impedance over time during a cryotreatment procedure with the pulmonary vein is occluded.
Figure 6B:
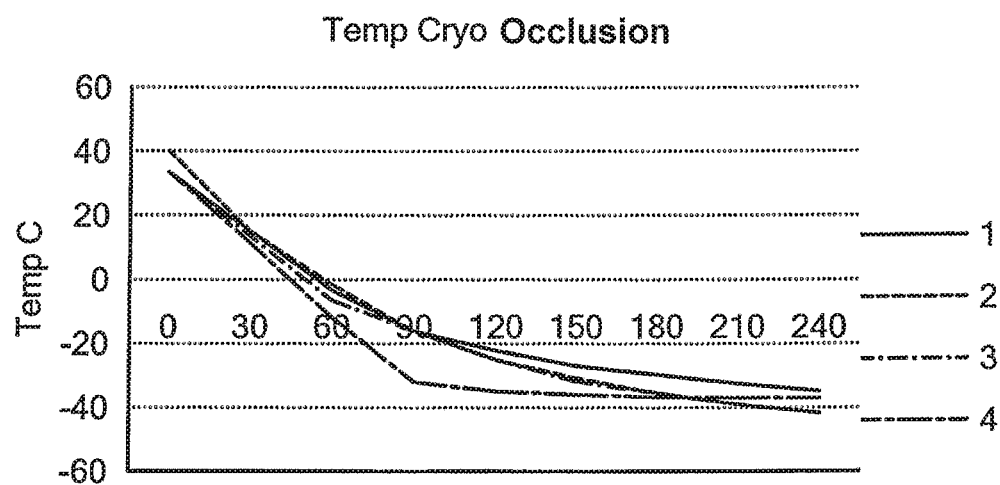
FIG. 6B shows a graph illustrating a change in temperature over time during a cryotreatment procedure with the pulmonary vein occluded.
Figure 6C:
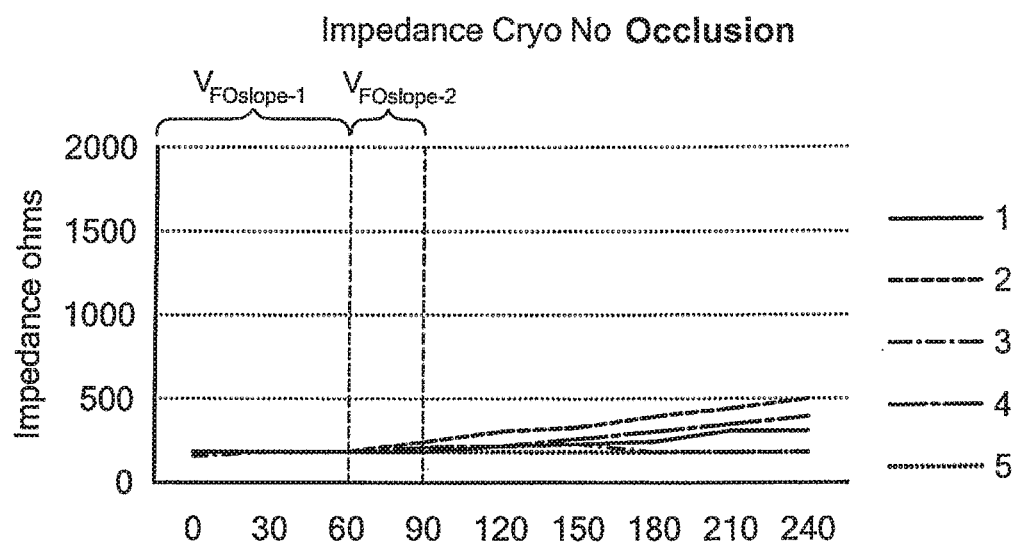
FIG. 6C shows a graph illustrating change in impedance over time during a cryotreatment procedure with the pulmonary vein not occluded.
Figure 6D:
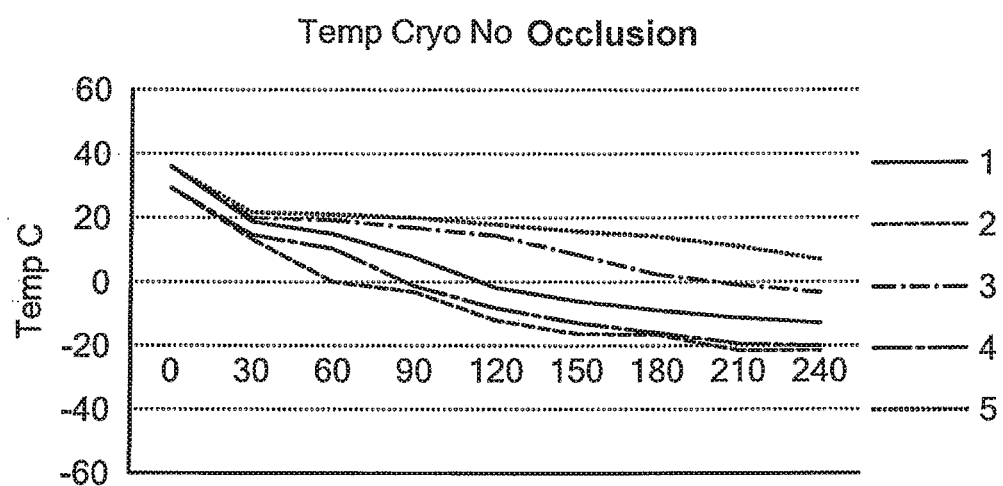
FIG. 6D shows a graph illustrating a change in temperature over time during a cryotreatment procedure with the pulmonary vein not occluded.
Figure 7:
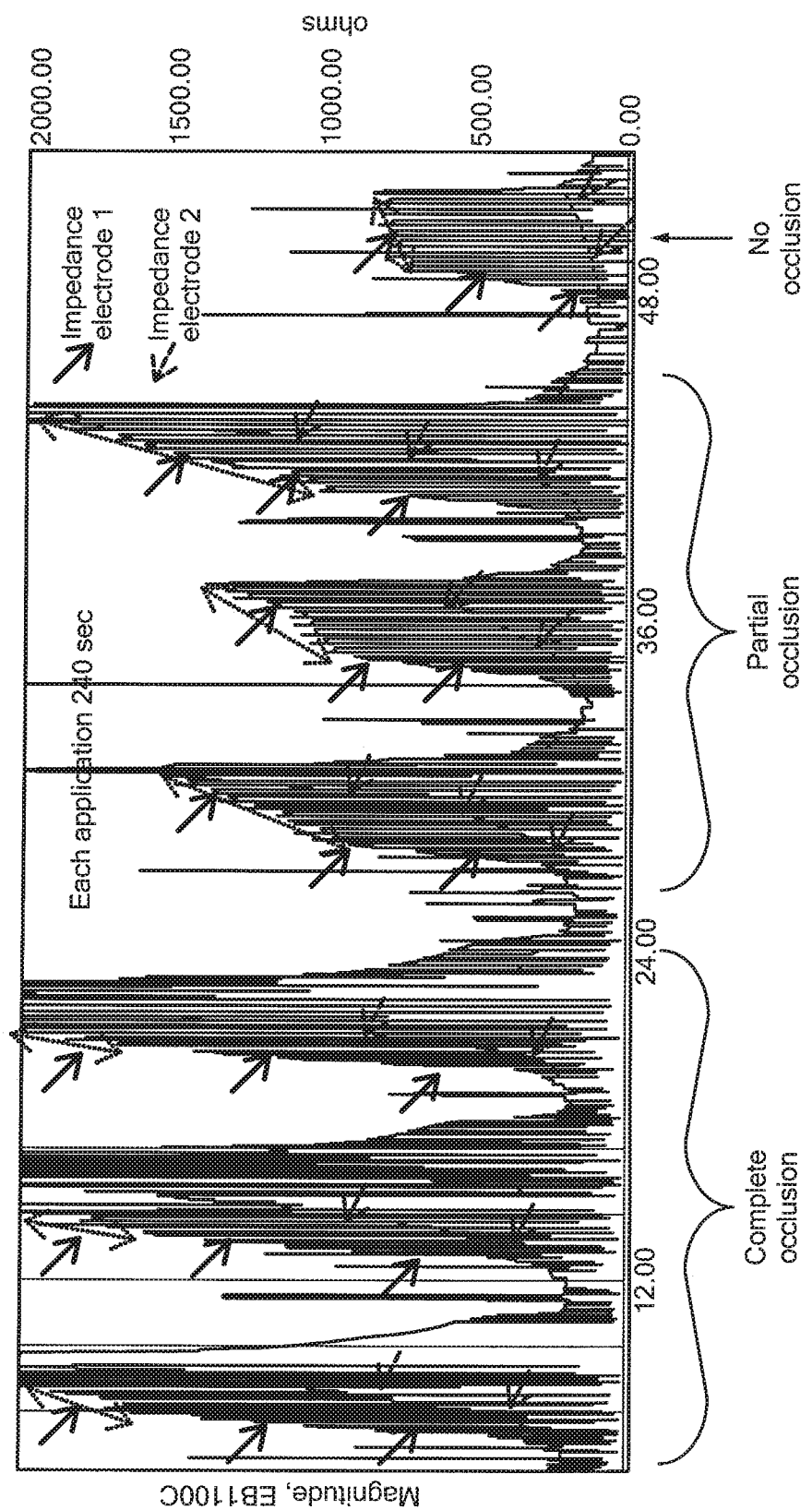
FIG. 7 shows a graph illustrating change in impedance over time during a cryotreatment procedure with the pulmonary vein completely occluded, partially occluded, and not occluded.

Referring now to FIGS. 6A-7, graphs illustrating the change in impedance and temperature over time are shown. The graphs show in FIGS. 6A-6D show non-limiting, experimental data. Each line in the charts (lines 1-4 in FIGS. 6A and 6B, and lines 1-5 in FIGS. 6C and 6D) is a unique set of test data. Impedance changes during cryoablation may be correlated to the ice thickness at the distal portion of the cryoballoon 26 (the thickness of the ice covering the distal electrode 30), which is directly related to the ice formation occurring at the perimeter of the cryoballoon 26. The processor 56 of the console computer 52 may be programmed or programmable to execute an algorithm for this correlation and display the results to the user. For example, based on impedance measurements, the computer 52 may display to the user text, graphical icons, or other indicia indicating complete or partial PV occlusion or lack of PV occlusion, which may indicate lesion quality. If the impedance immediately increases (as shown in FIG. 6A), this may indicate that the PV ostium is occluded and the freeze will be of high quality (that is, the PV ostium lesion will be circumferential and permanent). The duration of the cryoablation may be defined by the thickness of the surrounding myocardium and the impedance rise required to create ice across the entire thickness of the myocardium. As shown in FIG. 6A, complete occlusion may cause the impedance to rise rapidly with temperature crossing the 0° C. mark beginning at approximately 60 seconds into the cryoablation procedure. Impedance may continue to rise to 2000Ω (ohms) or above and temperature may decrease to approximately −37.8±3.3° C. at 120±30 seconds. If the impedance rise is delayed, on the other hand, this may indicate that an ice bridge was required to close a gap that had been allowing blood to flow past the distal portion of the cryoballoon 26. The impedance rise and time may then be adjusted to accommodate for this delay. Finally, if the impedance does not rise or is substantially delayed (as shown in FIG. 6C), this may indicate that the quality of the freeze is low because blood is flowing past the tip of the balloon, preventing the creation of a permanent, circumferential lesion. In this situation, the user may choose to stop the cryoablation and/or reposition the cryoballoon 26. As shown in FIG. 6C, impedance may not rise above 500Ω, with the temperature reaching only approximately −9.2±12.1° C. Ice thickness may grow significantly starting at approximately 60 seconds into the cryoablation before stabilizing at a thickness of approximately 3±0.5 mm. As shown in FIGS. 6B and 6D, temperature trends may follow impedance trends, with a sharp decrease and lower possible temperature being reached with full occlusion (as shown in FIG. 6B) and a less defined decrease and warmer possible temperature being reached with no occlusion (as shown in FIG. 6D).

Impedance and temperature measurements by one or more electrodes proximate the balloon, such as the distal electrode 30 of the device shown in FIG. 3 or the proximal electrode shown in FIG. 2, may be correlated to ice thickness, which, in turn, may be correlated to occlusion and lesion quality. Further, impedance may continue to rise even after ice formation. Monitoring this impedance during a cryotreatment procedure (that is, during the circulation of cryogenic fluid within the cryoballoon 26) may help an operator to determine when to stop the cryotreatment procedure. For example, the measured impedance may rise to approximately 2000Ω within approximately two or three minutes. An impedance value above this level, associated with a longer treatment time, may indicate that the cryotreatment procedure may be causing collateral damage to non-target tissue.

FIG. 7 shows change in impedance with full occlusion, partial occlusion, and no occlusion. The distal 30 and proximal 31 electrodes referred to in discussing FIG. 7 may be configured as shown, for example, in FIG. 2, wherein the proximal electrode 31 is distal to the balloon 26, between the distal electrode and the balloon 26. However, it will be understood that similar measurements may be recorded by the distal 30 and proximal 31 electrodes configured as shown in FIGS. 2 and 4. Thus, in the exemplary curves shown in FIG. 7, the proximal electrode 30 may be located closer to the balloon than the distal electrode 30 and will therefore be more thermally affected by the balloon.

The shape of the impedance curve may provide useful information regarding the quality of the freeze (for example, the curve timing, initial and final slope, and peak). When the PV is fully occluded, ice will form rapidly and impedance will rise rapidly, reaching approximately 2000Ω within approximately two or three minutes (as measured by the proximal distal electrode 30). The impedance rise may be noted by the distal electrode 30 within approximately 90 seconds. As shown in FIG. 7, the slope of impedance measured by both the distal electrode 30 and the proximal electrode 31 is positive. The slope of impedance measured by the proximal electrode 31 may include a first phase (referred to as $V_{FOslope-1}$) having a first slope measured between approximately 0 seconds and approximately 60 seconds (±10 seconds) and a second phase as the ice ball expands (referred to as $V_{FOslope-2}$) having a second slope measured between approximately 60 seconds and approximately 90 seconds (±10 seconds). In the non-limiting test 4 data shown in FIG. 6A, the slope of the first phase first phase (between approximately 0 seconds and approximately 60 seconds) is less than the slope of the second phase (between approximately 60 seconds and approximately 90 seconds. In the first phase, the rate of impedance increase is approximately 200Ω/minute (±100Ω), which may be used as a first reference slope, and this rate then increases to approximately 2000Ω/minute (±100Ω), which may be used as a second reference slope, in the second phase. This is indicative good ice ball formation. Further, impedance measured after the second phase, for example, between approximately 90 seconds and approximately 180 seconds (±10 seconds) may plateau, as shown in test 4 data in FIG. 6A. This may indicate that no further ice ball formation will take place. Measured slopes in the first and second phases may be compared to the first and second reference slopes that are indicative of good occlusion and, therefore, good lesion quality. As discussed below, the rate of impedance increase in both the first and second phases when there is poor occlusion may be approximately 200Ω/minute, and the rate of impedance increase with partial occlusion may be approximately 200Ω/minute in the first phase and approximately 1000Ω/minute in the second phase. However, it will be understood that these rates are exemplary, and may vary by patient.

Upon termination of cryoablation, the impedance sensed by the distal electrode 30 may initially decrease in the same way as the impedance sensed by the proximal electrode 31. The distal electrode 30 may recover faster than the proximal electrode 31 since the distal electrode 30 is less thermally affected by the balloon.

When the PV is partially occluded, the impedance increase, slope $V_{POslope-1}$, may be similar to that ($V_{FOslope-1}$) when the PV is completely occluded. As a non-limiting example, the rate of impedance increase may be approximately 200Ω/minute (±100Ω). However, the slope of the second phase ($V_{POslope-2}$) measured by the proximal electrode 31 may be slower that when there is full occlusion ($V_{FOslope-2}$), suggesting a slower ice expansion when the PV is partially occluded. As a non-limiting example, the rate of impedance increase in the second phase with full occlusion may be approximately 2000Ω/minute (±100Ω), whereas the rate of impedance increase in the second phase with only partial occlusion may be only approximately 1000Ω/minute (±100Ω). Blood may flow past the balloon with partial occlusion, and therefore the ice may reach the distal electrode 30 more slowly and the rate of impedance increase sensed by the distal electrode 30 may also be slower because it may take time for the ice to reach the distal electrode 30. However, the rate of ice expansion from the balloon to the proximal electrode 31 to the distal electrode 30 when the PV is completely occluded may be faster than when the PV is partially occluded. When the PV is not occluded, ice may not reach the distal electrode 30 at all. The distance the ice travels from the balloon (for example, as measured by the electrodes 30, 31) may indicate ice thickness. If ice thickness reaches approximately 3 mm, complete occlusion and, therefore, good lesion quality, may be indicated. Likewise, an increase in impedance to at least 2000 ohms (Ω) may also indicate complete occlusion and, as a result, good lesion quality. Impedance may be continuously during the cryotreatment procedure, even after the distal electrodes become covered in ice.

When the PV is not occluded, the initial impedance rise, $V_{NOslope-1}$, may be the same as with complete or partial occlusion ($V_{FOslope-1}$ and $V_{POslope-1}$, respectively); however, the first phase, $V_{NOslope-1}$, may be followed by a slow second phase, $V_{NOslope-2}$ (which may be even slower than the second phase, $V_{POslope-2}$, than when the PV is partially occluded) and the impedance sensed by the distal electrode 30 may rise very slowly. Non-limiting examples of the similarity between the first phase, $V_{NOslope-1}$, and the second phase, $V_{POslope-2}$, with no occlusion is shown in FIG. 6C. In all five tests, the slope of the second phase is very similar to the slope of the first phase. As a non-limiting example, the rate of increase in both the first and second phases may be approximately 200Ω/minute (±100Ω). The recovery phase may be similar for both electrodes 30, 31. When the ice expansion is very slow and limited, the total impedance rise may be lower (as shown by the smallest curve in FIG. 7) and the rate of ice expansion in the second phase may be limited. For example, if the second phase is flat or nearly flat, this may indicate that no further ice expansion will take place.

Figure 8A:
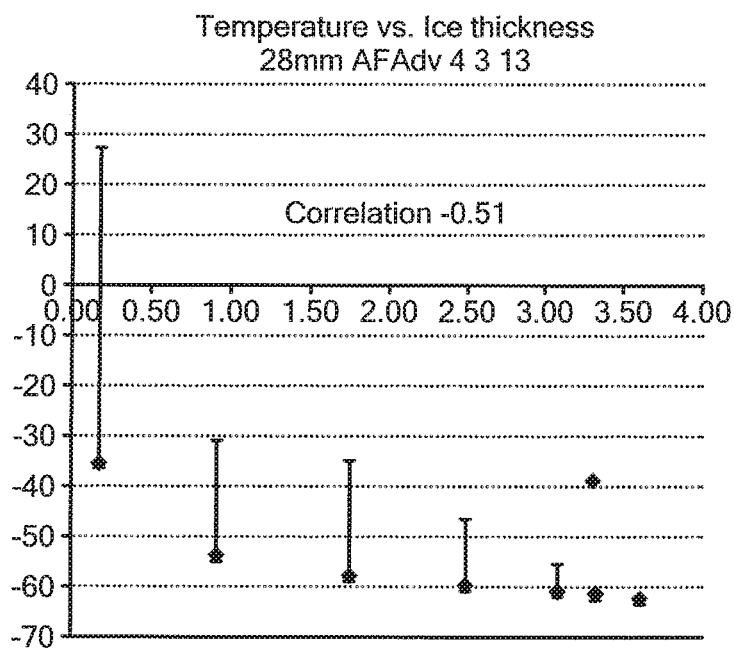
FIGS. 8A and 8B show graphs representing temperature and impedance measurements plotted against ice thickness.
Figure 8B:
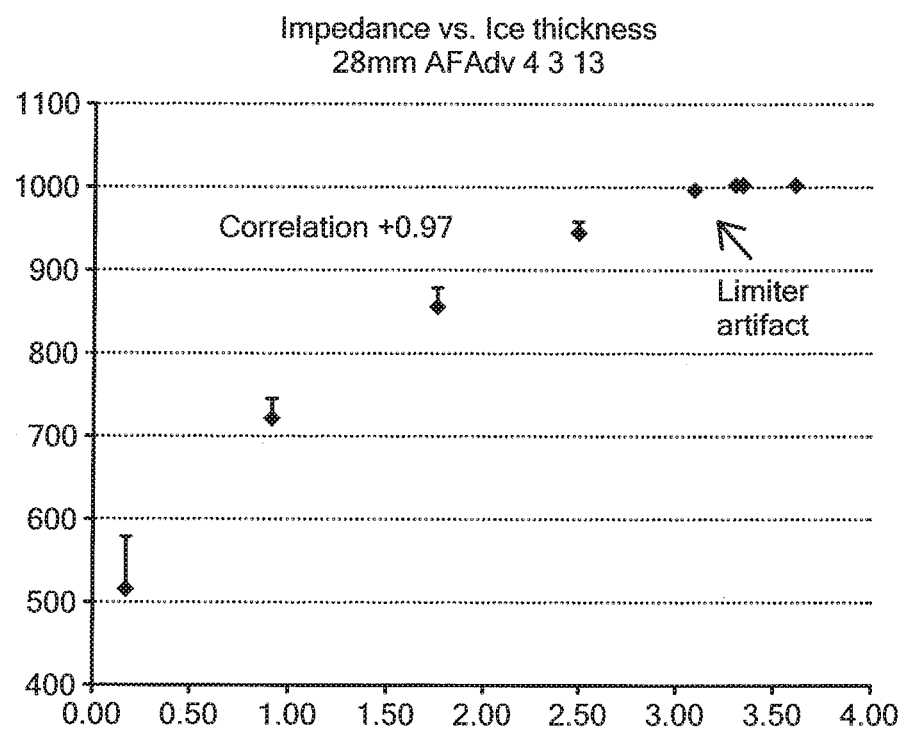

FIGS. 8A and 8B show graphs representing temperature and impedance measurements plotted against ice thickness. As is shown, ice thickness increases as temperature decreases, but at a certain temperature, ice thickness plateaus. As is further shown, as ice thickness increases, impedance increases.

Figure 9:
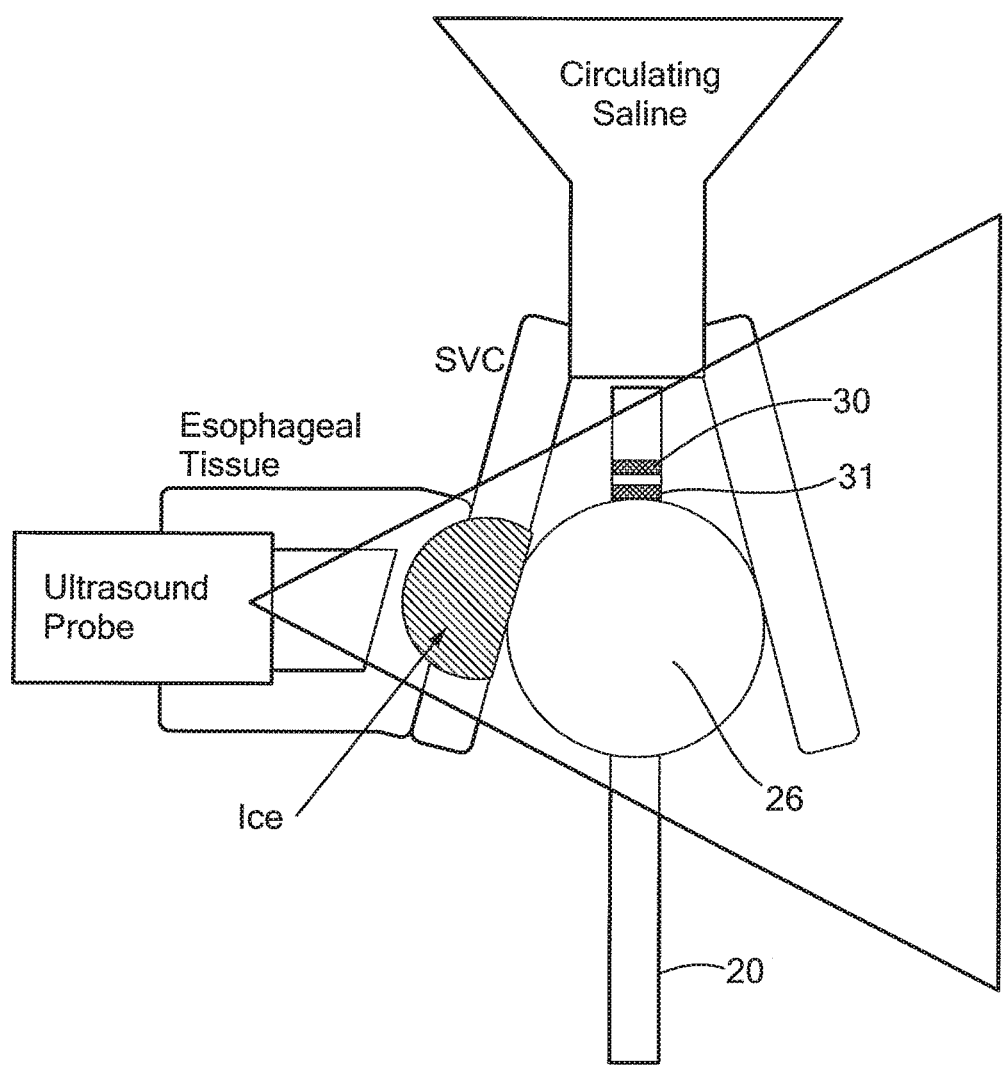
FIG. 9 shows a schematic representation of an experimental setup for correlating ice formation with impedance.

It may be concluded that ice thickness correlates with impedance if full occlusion is present. Further, PV isolation (that is, the formation of a permanent, circumferential lesion) may be achieved with approximately 3 mm of ice formation and an impedance rise of more than 2000 ohms. Ice thickness may be determined and/or confirmed using techniques such as ultrasound. An experimental setup such as that shown in FIG. 9 (stylized representation shown) may be used to correlate ice formation with impedance. For example, a cryotreatment device 12 including a proximal 31 and distal 30 electrodes may be inserted into a tissue sleeve, such as the superior vena cava of the heart. Saline having a temperature of approximately 37° C. may be circulated through the tissue sleeve toward the cryoballoon 26. As the cryoablation procedure is conducted, impedance and temperature may be continuously monitored. Further, an ultrasound probe may be used to evaluate the thickness of ice forming in the tissue sleeve. The ice thickness may then be correlated to the impedance measurements.

Impedance changes may also be combined with measurements such as time to response, time to electrogram disappearance (as recorded by the mapping catheter 16 and/or the distal 30 and proximal 31 electrodes), and/or rate of change in temperature in order to further improve the system's ability to evaluate PV occlusion and, therefore, lesion quality. Additionally, impedance changes may be combined with pressure changes to further improve the system's ability to evaluate PV ablation and occlusion. In such a case, the cryotreatment device 12 may further include one or more pressure sensors at various locations on the device and/or within the cryoballoon 26. Additionally, a quadrapolar impedance measurement electrode configuration may be used to remove contact of the electrode with tissue as a confusing factor.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention.

What is claimed is:

1. A cryoablation device, comprising:
   an elongate body having a proximal portion and a distal portion opposite the proximal portion;
   an expandable element coupled to the distal portion of the elongate body;
   a first electrode disposed proximal to the expandable element, the first electrode being a reference electrode;
   a shaft disposed distal to the expandable element;
   a shaft disposed distal to the expandable element;
   a plurality of discrete electrodes disposed circumferentially about the shaft, each of the plurality of discrete electrodes being spaced a distance apart; and
   at least one thermocouple disposed distal to the first electrode.

2. The device of claim 1, wherein the expandable element is a cryoballoon.

3. The device of claim 1, wherein the plurality of discrete electrodes are four discrete electrodes spaced an equal distance apart from one another.

4. The device of claim 1, wherein the plurality of discrete electrodes are disposed immediately distal to the expandable element.

5. The device of claim 4, wherein each of the plurality of discrete electrodes abut the expandable element.

6. The device of claim 1, wherein the at least one thermocouple is disposed 2 mm distal to the plurality of discrete electrodes.

7. The device of claim 1, further including a longitudinal axis, the plurality of discrete electrodes being radially arranged about the longitudinal axis.

8. The device of claim 1, wherein the at least one thermocouple is disposed proximate to the plurality of discrete electrodes.

9. The device of claim 1, wherein the first electrode is disposed circumferentially about the expandable element.

10. A system for cryoablating tissue, comprising:
    a cryoablation device, including:
        an elongate body having a proximal portion and a distal portion opposite the proximal portion;
        a cryoballon coupled to the distal portion of the elongate body;
        a first electrode disposed proximal to the cryoballon, the first electrode being a reference electrode;
        a shaft disposed distal to the cryoballon;
        a plurality of discrete electrodes disposed circumferentially about the shaft, each of the plurality of discrete electrodes being spaced a distance apart; and
        at least one thermocouple disposed distal to the first electrode;
    a console including a processor, the processor configured to:
        receive impedance measurements recorded by the first electrode and the plurality of discrete electrodes;
        receive temperature measurements recorded by the at least one thermocouple;
        compare impedance measured by the first electrode and the plurality of discrete electrodes; and
        determine if the cryoballoon is creating a permanent lesion, the determination being based upon at least one of the impedance measurement of the first electrode, the impedance measurement of the plurality of discrete electrodes, and the temperature measurement by the at least one thermocouple.

11. The system of claim 10, wherein the plurality of discrete electrodes are four discrete electrodes spaced an equal distance apart from one another.

12. The system of claim 11, wherein the plurality of discrete electrodes are disposed immediately distal to the cryoballoon.

13. The system of claim 12, wherein each of the plurality of discrete electrodes abut the cryoballoon.

14. The system of claim 10, wherein the processor is further configured to compare impedance measured by the first electrode to impedance measured by the plurality of discrete electrodes.

15. The system of claim 10, wherein the processor is further configured to individually monitor each of the plurality of discrete electrodes and evaluate a symmetry of the impedance measurements from each of the plurality of discrete electrodes.

16. The system of claim 10, wherein the at least one thermocouple is disposed 2 mm distal to the plurality of discrete electrodes.

17. The system of claim 10, wherein the first electrode is disposed circumferentially about the cryoballoon.

18. A system for cryoablating tissue, comprising:
    a cryoablation device, including:
        an elongate body having a proximal portion and a distal portion opposite the proximal portion;
        a cryoballoon coupled to the distal portion of the elongate body;
        a reference electrode disposed proximal to the cryoballoon and disposed circumferentially about the cryoballoon;
        a shaft disposed distal to the cryoballoon;
        four discrete electrodes disposed circumferentially about the shaft, each of the four discrete electrodes being spaced an equal distance apart, and each of the four discrete electrodes abutting the cryoballoon; and at least one thermocouple disposed distal to the reference electrode and disposed 2 mm distal to the four discrete electrodes;
  a console including a processor, the processor configured to:
    receive impedance measurements recorded by the reference electrode and the four discrete electrodes;
    receive temperature measurements recorded by the at least one thermocouple;
    compare impedance measured by the reference electrode and the four discrete electrodes; and
    determine if the cryoballoon is creating a permanent lesion, the determination being based upon at least one of the impedance measurement of the reference electrode, the impedance measurement of the four discrete electrodes, and the temperature measurement by the at least one thermocouple.

* * * * *